United States Patent
Tsunoda

(10) Patent No.: US 7,315,755 B2
(45) Date of Patent: Jan. 1, 2008

(54) SYSTEMS AND METHODS FOR COMMUNICATING A PROTOCOL OVER A NETWORK

(75) Inventor: Toshio Tsunoda, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 440 days.

(21) Appl. No.: 10/202,142

(22) Filed: Jul. 23, 2002

(65) Prior Publication Data

US 2003/0023155 A1 Jan. 30, 2003

(30) Foreign Application Priority Data

Jul. 25, 2001 (JP) ............................. 2001-224433

(51) Int. Cl.
A61B 5/00 (2006.01)
(52) U.S. Cl. ...................... 600/407; 128/920; 128/922; 128/923; 128/924; 705/2
(58) Field of Classification Search ................ 600/407, 600/408, 410, 420, 437, 300–1; 705/2, 3; 709/247, 223, 219; 324/309; 725/115, 114; 707/2, 3, 10, 104.1, 201; 128/922–4
See application file for complete search history.

(56) References Cited

U.S. PATENT DOCUMENTS

| | | | |
|---|---|---|---|
| 5,715,823 A * | 2/1998 | Wood et al. ................ | 600/437 |
| 5,742,905 A | 4/1998 | Pepe et al. | |
| 5,838,919 A | 11/1998 | Schwaller et al. | |
| 5,881,237 A | 3/1999 | Schwaller et al. | |
| 5,913,164 A | 6/1999 | Pawa et al. | |
| 5,937,165 A | 8/1999 | Schwaller et al. | |
| 5,991,816 A * | 11/1999 | Percival et al. ............ | 709/247 |
| 6,061,725 A | 5/2000 | Schwaller et al. | |
| 6,161,008 A | 12/2000 | Lee et al. | |
| 6,195,329 B1 | 2/2001 | Kawashima | |
| 6,289,234 B1 * | 9/2001 | Mueller ..................... | 600/410 |
| 6,304,753 B1 | 10/2001 | Hartmaier | |
| 6,351,773 B1 | 2/2002 | Fijolek et al. | |
| 6,374,295 B2 | 4/2002 | Farrow et al. | |

(Continued)

FOREIGN PATENT DOCUMENTS

JP 08-263570 10/1996

(Continued)

OTHER PUBLICATIONS

An English language translation of JP 2000-029971.

(Continued)

*Primary Examiner*—Eleni Mantis-Mercader
*Assistant Examiner*—Baisakhi Roy
(74) *Attorney, Agent, or Firm*—Armstrong Teasdale LLP

(57) ABSTRACT

The present invention aims at permitting numerous user terminals to share protocols as common resources. A vendor terminal or user terminal registers a pair of a protocol and a medical image, which is produced during scanning performed according to the protocol, by recording data in a protocol/medical image database included in a protocol management server. The user terminal acquires a medical image from the protocol management server over a network, and displays it on a display device. Moreover, the user terminal downloads a required protocol from the protocol management server and sets it in a medical diagnostic imaging system.

19 Claims, 7 Drawing Sheets

U.S. PATENT DOCUMENTS

| | | | |
|---|---|---|---|
| 6,393,478 B1 | 5/2002 | Bahlmann | |
| 6,438,690 B1 | 8/2002 | Patel et al. | |
| 6,678,703 B2 * | 1/2004 | Rothschild et al. | 707/201 |
| 2002/0029264 A1 * | 3/2002 | Ogino et al. | 709/223 |
| 2002/0091547 A1 * | 7/2002 | Ohe et al. | 705/2 |
| 2003/0005464 A1 * | 1/2003 | Gropper et al. | 725/115 |
| 2003/0088173 A1 * | 5/2003 | Kassai et al. | 600/408 |
| 2003/0195838 A1 * | 10/2003 | Henley | 705/37 |

FOREIGN PATENT DOCUMENTS

| | | |
|---|---|---|
| JP | 2000-029971 | 1/2000 |
| WO | WO 01/29688 A1 | 4/2001 |

OTHER PUBLICATIONS

An English language translation of JP 08-263570.

* cited by examiner

FIG. 2

PROTOCOL/MEDICAL IMAGE DATABASE
12

| PROTOCOL IDENTIFIER | DATE OF REGISTRATION | TYPE OF IMAGE | REGION | IMAGE DATA | GRADE | REGISTERING PERSON | PROTOCOL | |
|---|---|---|---|---|---|---|---|---|
| | | | | | | | SCANNING TECHNIQUE | IMAGING PARAMETERS |
| P001 | 2000-1-16 | MRI | HEART | 1110010100... | 80 | VENDOR | FSE | TR=2100, TE=70, ... |
| P002 | 2000-1-16 | MRI | LUNG | 1101001000... | 90 | VENDOR | GE | TR=2400, TE=80, ... |
| P003 | 2000-2-20 | X-RAY CT | HEAD | 1111010011... | 70 | VENDOR | AXIAL SCAN | p=3, th=1... |
| P004 | 2000-2-20 | X-RAY CT | ABDOMEN | 0111010001... | 60 | HOSPITAL D | HELICAL SCAN | p=6, th=2... |
| P005 | 2000-3-20 | X-RAY CT | ABDOMEN | 1100100101... | 70 | HOSPITAL D | GANTRY-TILTED HELICAL SCAN | p=2, th=3... |
| P006 | 2000-5-10 | MRI | LIVER | 1101101001... | 70 | HOSPITAL B | EPI | TR=1700, TE=60, ... |
| P007 | 2000-7-1 | MRI | LIVER | 0100111011... | 80 | HOSPITAL E | FRFSE | TR=2600, TE=75, ... |
| P008 | 2000-7-10 | MRI | PANCREA | 1101101101... | 90 | HOSPITAL A | EPI | TR=2300, TE=55, ... |
| P009 | 2000-9-20 | MRI | HEAD | 1101001011... | 60 | HOSPITAL A | FSE | TR=1500, TE=35, ... |
| P010 | 2000-10-20 | MRI | HEART | 0010110110... | 60 | HOSPITAL D | FSE | TR=2800, TE=70, ... |
| P011 | 2000-10-20 | MRI | NECK | 1101011011... | 80 | HOSPITAL B | FRFSE | TR=2500, TE=55, ... |
| P012 | 2000-11-20 | MRI | ABDOMEN | 0001110111... | 70 | HOSPITAL A | GE | TR=2100, TE=30, ... |

FIG. 3

SUBSCRIBER INFORMATION DATABASE 13

| PROTOCOL IDENTIFIER | PROTOCOL PERMISSION HOSPITAL A | DOWNLOAD PERMISSION HOSPITAL B | PERMISSION HOSPITAL C | ... |
|---|---|---|---|---|
| P001 | GRANTED | NOT GRANTED | GRANTED | |
| P002 | GRANTED | NOT GRANTED | GRANTED | |
| P003 | NOT GRANTED | NOT GRANTED | GRANTED | |
| P004 | NOT GRANTED | GRANTED | GRANTED | |

FIG. 7

DOWNLOAD WEB PAGE
G1

[USER=HOSPITAL A]
[INSTALLED MODALITY=MRI]

LIST OF PROTOCOLS THAT CAN BE DOWNLOADED

HOME

| DATE OF REGISTRATION | REGION | THUMBNAIL IMAGE | GRADE | REGISTERING PERSON | PROTOCOL ||
|---|---|---|---|---|---|---|
| | | | | | SCANNING TECHNIQUE | IMAGING PARAMETERS |
| 2000-1-16 | HEART | | 80 | VENDOR | FSE | TR=2100, TE=70,... T1=200, T2=300 |
| 2000-1-16 | LUNG | | 90 | VENDOR | GE | TR=2400, TE=80,... T1=150, T2=250 |
| 2000-5-10 | LIVER | | 70 | HOSPITAL B | EPI | TR=1700, TE=60,... T1=400, T2=600 |
| 2000-7-1 | LIVER | | 80 | HOSPITAL E | FRFSE | TR=2600, TE=75,... T1=50, T2=80 |

DOWNLOAD
DOWNLOAD
DOWNLOAD
DOWNLOAD

CONDITION RETRIEVAL         CANCEL

SYSTEMS AND METHODS FOR COMMUNICATING A PROTOCOL OVER A NETWORK

CROSS REFERENCE TO RELATED APPLICATIONS

This application claims the benefit of Japanese Application No. 2001-224433 filed Jul. 25, 2001.

BACKGROUND OF THE INVENTION

The present invention relates to a protocol/medical image registration method, a medical image provision method, a protocol utilization method, a protocol/medical image registration system, a medical image provision system, a protocol utilization system, a vendor terminal, a user terminal, and a protocol management server. More specifically, the present invention relates to a protocol/medical image registration method that permits centralized management of pairs of a protocol and a medical image, a medical image provision method that provides a user terminal with a medical image, a protocol utilization method that permits numerous user terminals to share protocols as common resources. Moreover, the present invention relates to systems in which the protocol/medical image registration method, medical image provision method, and protocol utilization method are implemented, and a vendor terminal, a user terminal, and a protocol management server to be adapted to the systems.

In general, sophisticated medical diagnostic imaging systems including a magnetic resonance imaging (MRI) system and an X-ray computed tomography (CT) system require setting of complex conditions for imaging which are referred to as a protocol. For example, in the case of the MRI system, a pulse sequence-related imaging technique such as the fast spin echo (FSE) technique, gradient echo (GE) technique, echo planar imaging (EPI) technique, or fast recovery fast spin echo (FRFSE) technique is set as a protocol. Otherwise, imaging parameters including a longitudinal relaxation time (T1), a transverse relaxation time (T2), a repetition time (TR), and an echo time (TE) are set as a protocol.

Conventionally, for every scanning, a physician or a paramedic manually enters a protocol in a medical diagnostic imaging system or sets a protocol, which is read from a portable storage medium, therein.

The problems described below underlie the foregoing conventional protocol setting method.

(1) It is labor-intensive and time-consuming to manually enter a protocol or procure a portable storage medium on which the latest protocol is saved.

(2) It takes much time to find out a protocol suitable for a region to be scanned (for example, the brain, heart, or lung) or a purpose of use (for example, identification of a tumor, discovery of morphologic abnormality, or assessment of perfusion). This is inefficient.

(3) Even if a protocol of great use value is devised, it is hard to share the protocol with other physicians and paramedics.

SUMMARY OF THE INVENTION

Therefore, the first object of the present invention is to provide a protocol/medical image registration method and system that permit management of pairs of a protocol and a medical image on a centralized basis.

The second object of the present invention is to provide a medical image provision method and system that provide a user terminal with a medical image produced using a certain protocol.

The third object of the present invention is to provide a protocol utilization method and system that permit numerous user terminals to utilize protocols as common resources.

The fourth object of the present invention is to provide a vendor terminal, a user terminal, and a protocol management server to be adapted to the protocol/medical image registration method and system, medical image provision method and system, and protocol utilization method and system.

According to the first aspect of the present invention, there is provided a protocol/medical image registration method. Herein, a vendor terminal managed by a vendor and a protocol management server are connected to each other. If new registration of or update or a protocol and a medical image produced using the protocol is requested at the vendor terminal, a new registration request or an update request is sent to the protocol management server. In response to the registration request, the protocol management server newly registers or updates the protocol and medical image sent from the vendor terminal by recording data in a database.

In the protocol/medical image registration method according to the first aspect, pairs of a protocol and a medical image sent from the vendor terminal can be efficiently managed on a centralized basis using the database included in the protocol management server.

According to the second aspect of the present invention, there is provided a protocol/medical image registration method. Herein, a protocol management server and a plurality of user terminals are interconnected over a network. If new registration of or update of a protocol and a medical image produced using the protocol is requested at a user terminal, a new registration request or an update request is sent to the protocol management server. In response to the registration request, the protocol management server newly registers or updates the protocol and medical image sent from the user terminal by recording data in a database.

In the protocol/medical image registration method according to the second aspect, pairs of a protocol and a medical image sent from the user terminals over the network are efficiently managed on a centralized basis using the database included in the protocol management server.

According to the third aspect of the present invention, there is provided a protocol/medical image registration method based on the aforesaid protocol/medical image registration method, a vendor or a third person evaluates the use value of a protocol newly registered or updated using the database. The user of a user terminal who has registered the protocol is paid a reward dependent on the result of evaluation.

In the protocol/medical image registration method according to the third aspect, a registering person (that is, the user of a user terminal who has registered the protocol using the database) is paid a reward dependent on the use value of the protocol. It is therefore possible to motivate people to develop or register a protocol of great use value.

According to the fourth aspect of the present invention, there is provided a protocol/medical image registration method based on the aforesaid protocol/medical image registration method. Herein, the medical image is at least one of an MRI image, an X-ray CT image, an ultrasonic image, a PET image, a radiographic image, and a CR image.

In the protocol/medical image registration method according to the fourth aspect, protocols for use in producing various kinds of medical images (MRI images, X-ray CT images, ultrasonic images, PET images, radiographic images, and CR images) that prove very useful in clinical practice can be registered.

According to the fifth aspect of the present invention, there is provided a protocol/medical image registration method based on the aforesaid protocol/medical image registration method. Herein, when the medical image is an MRI image, the protocol refers to at least one of a pulse sequence-related imaging technique and imaging parameters.

In the protocol/medical image registration method according to the fifth aspect, a pulse sequence-related imaging technique or imaging parameters that greatly affects a scan time or the properties of MRI images can be registered as a protocol.

According to the sixth aspect of the present invention, there is provided a medical image provision method. Herein, if display of medical images registered according to the aforesaid protocol/medical image registration method is requested at a user terminal, an image request is sent to a protocol management server. In response to the request, the protocol management server reads the medical image from a database, and transmits it to the user terminal. The user terminal receives the medical image and displays it on a screen included therein.

In the medical image provision method according to the sixth aspect, a medical image received from the protocol management server can be displayed on a screen included in a user terminal. Consequently, a protocol used to produce the medical image can be evaluated.

According to the seventh aspect of the present invention, there is provided a protocol utilization method. Herein, if utilization of a protocol registered according to the aforesaid protocol/medical image registration method is requested at a user terminal, a protocol download request is sent to a protocol management server. In response to the protocol download request, the protocol management server reads the protocol from a database and transmits it to the user terminal. The user terminal receives the protocol and sets it in a medical diagnostic imaging system.

In the protocol utilization method according to the seventh aspect, a user terminal acquires a protocol of great use value from the protocol management server. The protocol can be set in a medical diagnostic imaging system without the necessity of time-consuming work.

According to the eighth aspect of the present invention, there is provided a protocol utilization method. Herein, a medical image registered according to the aforesaid protocol/medical image registration method is sent from a protocol management server to a user terminal, and displayed on a screen included in the user terminal. Moreover, if utilization of the protocol is requested at the user terminal, a protocol download request is sent to the protocol management server. In response to the protocol download request, the protocol management server reads the protocol from the database, and transmits it to the user terminal. The user terminal sets the received protocol in a medical diagnostic imaging system.

In the protocol utilization method according to the eighth aspect, a medical image acquired from the protocol management server is displayed on the screen included in the user terminal. Whether a protocol is worth being utilized can be judged readily. If necessary, a protocol of great use value can be acquired from the protocol management server and set in a medical diagnostic imaging system without the necessity of time-consuming work.

According to the ninth aspect of the present invention, there is provided a protocol utilization method based on the aforesaid protocol utilization method. Herein, the user of a user terminal who has received a protocol is charged a use fee dependent on the number of times by which the protocol is downloaded.

In the protocol utilization method according to the ninth aspect, a user pays a use fee dependent on the number of times by which a protocol is downloaded. Consequently, a service provider can collect a fee dependent on the cost of service provision.

According to the tenth aspect of the present invention, there is provided a protocol utilization method based on the aforesaid protocol utilization method. Herein, the user of a user terminal who has received a protocol is charged a use fee dependent on the number of times by which the protocol is used.

In the protocol utilization method according to the tenth aspect, a user pays a use fee dependent on the number of times by which the protocol is used (the number of times by which scanning is performed). Consequently, a service provider can collect a fee dependent on the convenience the user enjoys.

According to the eleventh aspect of the present invention, there is provided a protocol utilization method based on the aforesaid protocol utilization method. Herein, the user of a user terminal who has registered the protocol is paid a reward dependent on the use fee.

In the protocol utilization method according to the eleventh aspect, a registering person can continuously receive a reward dependent on the use record of a protocol.

According to the twelfth aspect of the present invention, there is provided a protocol utilization method based on the aforesaid protocol utilization method. Herein, protocols to be sent to the user terminals over the network are protocols having at least one of the term of validity thereof and the number of times of use thereof limited.

In the protocol utilization method according to the twelfth aspect, a protocol having the term of validity thereof or the number of times of use thereof limited is transmitted to a user terminal. This would prove helpful in using a protocol by way of trial or temporarily.

According to the thirteenth aspect of the present invention, there is provided a protocol/medical image registration system consisting mainly of a vendor terminal that is managed by a vendor and a protocol management server connected to the vendor terminal. If an operator instructs new registration of or update of a protocol and a medical image produced using the protocol, the vendor terminal transmits a new registration request or an update request to the protocol management server. In response to the registration request, the protocol management server newly registers or updates the protocol and medical image sent from the vendor terminal by recording data in a database.

In the protocol/medical image registration system according to the thirteenth aspect, the protocol/medical image registration method according to the first aspect can be implemented preferably.

According to the fourteenth aspect of the present invention, there is provided a protocol/medical image registration system consisting mainly of a protocol management server, a plurality of user terminals, and a network over which the protocol management server and user terminals are interconnected. If an operator instructs new registration of or update of a protocol and a medical image produced using the protocol, the user terminal transmits a new registration request or an update request to the protocol management server. In response to the registration request, the protocol management server newly registers or updates the protocol and medical image sent from the user terminal by recording data in a database.

In the protocol/medical image registration system according to the fourth aspect, the protocol/medical image registration method according to the second aspect can be implemented preferably.

According to the fifteenth aspect of the present invention, there is provided a medical image provision system consisting mainly of a vendor terminal managed by a vendor, a protocol management server connected to the vendor terminal, a plurality of user terminals, and a network over which the protocol management server and user terminals are interconnected. If an operator instructs new registration of or update of a protocol and a medical image produced using the protocol, the vendor terminal or user terminal transmits a new registration request or an update request to the protocol management server. In response to the registration request, the protocol management server newly registers or updates the protocol and medical image sent from the vendor terminal or user terminal. If an operator instructs acquisition of the medical image, the user terminal transmits an image request to the protocol management server. In response to the image request, the protocol management server reads the medical image from the database, and transmits it to the user terminal. The user terminal receives the medical images and displays it on a screen included therein.

In the medical image provision system according to the fifteenth aspect, the medical image provision method according to the sixth aspect can be implemented preferably.

According to the sixteenth aspect of the present invention, there is provided a protocol utilization system consisting mainly of a vendor terminal managed by a vendor, a protocol management server connected to the vendor terminal, a plurality of user terminals, and a network over which the protocol management server and user terminals are interconnected. If an operator instructs new registration of or update of a protocol and a medical image produced using the protocol, the vendor terminal or user terminal transmits a new registration request or an update request to the protocol management server. In response to the registration request, the protocol management server newly registers or updates the protocol and medical image sent from the vendor terminal or user terminal by recording data in a database. If an operator instructs utilization of the protocol, the user terminal transmits a protocol download request to the protocol management server. In response to the protocol download request, the protocol management server reads the protocol from the database and transmits it to the user terminal. The user terminal sets the received protocol in a medical diagnostic imaging system.

In the protocol utilization system according to the sixteenth aspect, the protocol utilization method according to the seventh aspect is implemented preferably.

According to the seventeenth aspect of the present invention, there is provided a protocol utilization system consisting mainly of a vendor terminal managed by a vendor, a protocol management server connected to the vendor terminal, a plurality of user terminals, and a network over which the protocol management server and user terminals are interconnected. If an operator instructs new registration of or update of a protocol and a medical image produced using the protocol, the vendor terminal or user terminal transmits a new registration request or an update request to the protocol management server. In response to the registration request, the protocol management server newly registers or updates the protocol and medical image sent from the vendor terminal or user terminal by recording data in a database. If an operator instructs acquisition of the medical image, the user terminal transmits an image request to the protocol management server. In response to the image request, the protocol management server reads the medical image from the database and transmits it to the user terminal. The user terminal receives the medical image and displays it on a screen included therein. If an operator instructs utilization of the protocol, the user terminal transmits a protocol download request to the protocol management server. In response to the protocol download request, the protocol management server reads the protocol from the database and transmits it to the user terminal. The user terminal sets the received protocol in a medical diagnostic imaging system.

In the protocol utilization system according to the seventeenth aspect, the protocol utilization method according to the eighth aspect can be implemented preferably.

According to the eighteenth aspect of the present invention, there is provided a protocol utilization system based on the aforesaid protocol utilization system. Herein, a protocol download history or a protocol use history is recorded in the user terminal having received the protocol.

In the protocol utilization system according to the eighteenth aspect, the protocol download history or use history is recorded in a user terminal. This facilitates later analysis of the use record of a protocol.

According to the nineteenth aspect of the present invention, there is provided a protocol utilization system based on the aforesaid protocol utilization system. Herein, the protocol management server successively accesses the user terminals over the network and receives the download history or use history.

In the protocol utilization system according to the nineteenth aspect, a user terminal need not actively transmit the download history or use history. Consequently, the use records of protocols can be preserved the protocol management server without an increase in the load on user terminals.

According to the twentieth aspect of the present invention, there is provided a protocol utilization system based on the aforesaid protocol utilization system, the user terminals transmit the download history or use history to the protocol management server over the network.

In the protocol utilization system according to the twentieth aspect, the user terminal actively transmits the download history or use history to the protocol management server. Consequently, the use records of protocols can be preserved in the protocol management server without an increase in the load on the protocol management server.

According to the twenty-first aspect of the present invention, there is provided a protocol utilization system based on the aforesaid protocol utilization system. Herein, a plurality of protocol management servers is included and the protocol management servers are accessible to the user terminals.

In the protocol utilization system according to the twenty-first aspect, the plurality of protocol management servers is accessible to the user terminals. Consequently, the protocol utilization system has become unsusceptible to a network failure or a system failure, and has the reliability improved. Moreover, if the protocol management servers that are accessed by the user terminals are changed depending on a load on the network, a communication time required for registration or download can be shortened.

According to the twenty-second aspect of the present invention, there is provided a protocol utilization system based on the aforesaid protocol utilization system. Herein, protocols that can be downloaded from the protocol management server are limited in compliance with the legal conditions established at the installation site of the user terminals.

In the protocol utilization system according to the twenty-second aspect, download of a protocol that does not comply with the legal conditions (for example, legislation and safety standards) established at the installation site of the user terminals can be prevented.

According to the twenty-third aspect of the present invention, there is provided a protocol utilization system based on the aforesaid protocol utilization system. Herein, when a protocol is newly registered or updated, the protocol management server notifies the user terminals of the fact over the network.

In the protocol utilization system according to the twenty-third aspect, the users of the user terminals can be notified the fact that a new protocol has been registered, and utilization of the new protocol can be facilitated.

According to the twenty-fourth aspect of the present invention, there is provided a protocol utilization system based on the aforesaid protocol utilization system. Herein, the protocol management server responds to a download request received from a user terminal at which no contract is made for the utilization of protocols but does not respond to a registration request received from the user terminal.

In the protocol utilization system according to the twenty-fourth aspect, the protocol management server responds to a download request received from a user terminal at which no contract is made. Consequently, a protocol utilization service can be provided for a large number of users. However, the protocol management server does not respond to a registration request (a new registration request or an update request) received from a user terminal at which a contract is not made. The contents of the database can be kept reliable.

According to the twenty-fifth aspect of the present invention, there is provided a protocol utilization system based on the protocol utilization system. Herein, the medical diagnostic imaging system is at least one of a magnetic resonance imaging (MRI) system, an X-ray computed tomography (CT) system, a diagnostic ultrasound system, a positron emission tomography (PET) system, a radiography system, and a computed radiography (CR) system.

In the protocol utilization system according to the twenty-fifth aspect, a protocol can be set in various medical diagnostic systems (MRI system, X-ray CT system, diagnostic ultrasound system, PET system, radiography system, and CR system) that prove very useful in clinical practice without the necessity of time-consuming work.

According to the twenty-sixth aspect of the present invention, there is provided a protocol utilization system based on the protocol utilization system. Herein, if the medical diagnostic imaging system is an MRI system, the protocol refers to at least one of a pulse sequence-related imaging technique and imaging parameters.

In the protocol utilization system according to the twenty-sixth aspect, a protocol that is a pulse sequence-related imaging technique or imaging parameters can be set in the MRI system.

According to the twenty-seventh aspect of the present invention, there is provided a vendor terminal that consists mainly of a registration request transmitting means and an object-of-registration transmitting means and that is managed by a vendor. If an operator instructs new registration or update of a protocol and a medical image produced using the protocol, the registration request transmitting means transmits a new registration request or an update request to a protocol management server. The object-of-registration transmitting means transmits the protocol and medical image, which should be registered, to the protocol management server.

In the vendor terminal according to the twenty-seventh aspect, a pair of a protocol and a medical image can be sent to the protocol management server and registered using a database.

According to the twenty-eighth aspect of the present invention, there is provided a user terminal consisting mainly of a registration request transmitting means and an object-of-registration transmitting means. If an operator instructs new registration or update of a protocol and a medical image produced using the protocol, the registration request transmitting means transmits a new registration request or an update request to a protocol management server over a network. The object-of-registration transmitting means transmits the protocol and medical image, which should be registered, to the protocol management server.

In the user terminal according to the twenty-eighth aspect, a pair of a protocol and a medical image produced using the protocol can be sent to the protocol management server over the network and registered using a database.

According to the twenty-ninth aspect of the present invention, there is provided a user terminal consisting mainly of an image request transmitting means and a medical image displaying means. If an operator instructs acquisition of a medical image, the image request transmitting means transmits an image request to a protocol management server over a network. The medical image displaying means receives the medical image from the protocol management server and displays it on a screen included in the user terminal.

In the user terminal according to the twenty-ninth aspect, a required medical image can be acquired and displayed on the screen.

According to the thirtieth aspect of the present invention, there is provided a user terminal consisting mainly of a protocol download request transmitting means and a protocol setting means. If an operator instructs utilization of a protocol, the protocol download request transmitting means transmits a protocol download request to a protocol management server over a network. The protocol setting means receives the protocol from the protocol management server and sets it in a medical diagnostic imaging system.

In the user terminal according to the thirtieth aspect, a protocol of great use value can be acquired from the protocol management server and set in a medical diagnostic imaging system without the necessity of time-consuming work.

According to-the thirty-first aspect of the present invention, there is provided a user terminal consisting mainly of a medical image displaying means, a protocol download request transmitting means, and a protocol setting means. The medical image displaying means receives a medical image from a protocol management server over a network, and displays it. If an operator instructs utilization of a protocol, the protocol download request transmitting means transmits a protocol download request to the protocol management server. The protocol setting means receives the protocol from the protocol management server and sets it in a medical diagnostic imaging system.

In the user terminal according to the thirty-first aspect, whether a protocol is worth being utilized can be readily judged at the sight of a medical image displayed on the screen. If necessary, a protocol of great use value can be acquired from the protocol management server and set in a medical diagnostic imaging system without the necessity of time-consuming work.

According to the thirty-second aspect of the present invention, there is provided a protocol management server having a database registering means. In response to a new registration request or an update request received from a vendor terminal or a user terminal, the database registering means newly registers or updates a protocol and a medical image, which are received from the vendor terminal or user terminal, by recording data in a database.

In the protocol management server according to the thirty-second aspect, a pair of a protocol and a medical image received from a vendor terminal or a user terminals can be registered by recording data in a database. Consequently, pairs of a protocol and a medical image can be efficiently managed on a centralized basis.

According to the thirty-third aspect of the present invention, the aforesaid protocol management server also includes a medical image transmitting means. In response to an image request received from a user terminal over a network, the medical image transmitting means reads a medical image from the database and transmits it to the user terminal.

In the protocol management server according to the thirty-third aspect, a medical image can be read from the database, sent to a user terminal, and displayed on a screen included in the user terminal.

According to the thirty-fourth aspect of the present invention, the aforesaid protocol management server also includes a protocol transmitting means. In response to a protocol download request received from a user terminal over a network, the protocol transmitting means reads a protocol from the database and transmits it to the user terminal.

In the protocol management server according to the thirty-fourth aspect, a protocol can be read from the database, sent to a user terminal, and set in a medical diagnostic imaging system.

In a protocol/medical image registration method and system according to the present invention, a pair of a protocol and a medical image sent from a vendor terminal or a user terminal can be registered by recording data in a database included in a protocol management server. Pairs of a protocol and a medical image can thus be managed on a centralized basis.

Moreover, since a registering person is given a monetary incentive, more and more protocols and medical images of great use value can be preserved in a protocol management server.

In a medical image provision method and system according to the present invention, a medical image acquired from a protocol management server can be displayed on a screen included in a user terminal.

In a protocol utilization method and system according to the present invention, protocols and medical images registered using a database included in a protocol management server can be shared by numerous user terminals.

Moreover, if utilization of a protocol and a medical image is provided as a pay service, a highly profitable business model can be constructed.

A vendor terminal, a user terminal, and a protocol management server in accordance with the present invention can be preferably adapted to the foregoing methods and systems.

Further objects and advantages of the present invention will be apparent from the following description of the preferred embodiments of the invention as illustrated in the accompanying drawings.

BRIEF DESCRIPTION OF THE DRAWINGS

FIG. 2 shows the structure of a protocol/medical image database.

FIG. 3 shows the structure of a customer information database.

FIG. 7 is an explanatory diagram concerning a download web page.

DETAILED DESCRIPTION OF THE INVENTION

The present invention will be described in conjunction with an illustrated embodiment.

Figure 1:
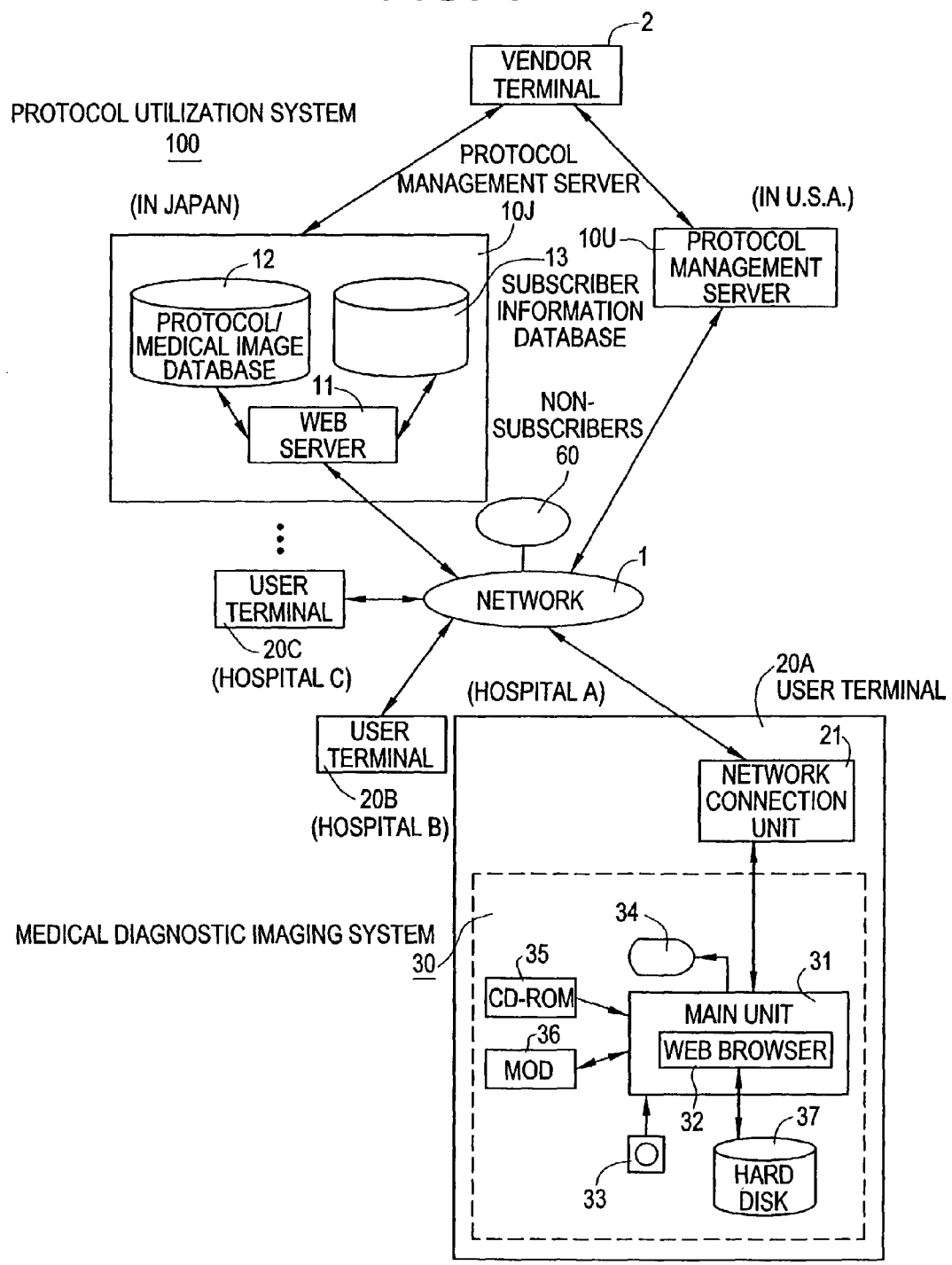
FIG. 1 is a block diagram showing a protocol utilization system in accordance with an embodiment of the present invention.

FIG. 1 is a block diagram showing a protocol utilization system 100 in accordance with an embodiment of the present invention. The protocol utilization system 100 has the capabilities of a protocol/medical image registration system and a medical image provision system.

The protocol utilization system 100 consists mainly of a vendor terminal 2, a network 1, protocol management servers 10J and 10U, and user terminals 20A, 20B, 20C, etc. The vendor terminal 2 is managed by a vendor. The network 1 may be a local area network (LAN), a wide area network (WAN) or the like. The protocol management servers 10J and 10U and the user terminals 20A, 20B, 20C, etc. are interconnected over the network 1. A transmission medium adopted for the network 1 may be radiocommunication or wire communication.

The protocol management server 10J is installed in, for example, Japan.

The protocol management server 10U is installed in, for example, the United States of America.

The user terminals 20A, 20B, and 20C are installed at hospitals A, B, and C.

If the network 1 is the Internet, non-subscribers 60 who have not contracted for the use of the protocol management servers 10J and 10U or non-subscriber terminals are also interconnected over the network 1.

From the viewpoint of security, preferably, the secure socket layer protocol (SSL) or the like is adopted.

The protocol management server 10J consists mainly of a web server 11, a protocol/medical image database 12, and a subscriber information database 13. The protocol management server 10U has the same components as the protocol management server 10J.

The user terminal 20A consists mainly of a network connection unit 21 connected on the network 1 and a medical diagnostic imaging system (for example, a magnetic resonance imaging (MRI) system, an X-ray computed tomography (CT) system, a diagnostic ultrasound system, a positron emission tomography (PET) system, a radiography system, or a computed radiography (CR) system) 30. The user terminals 20B and 20C have the same components as the user terminal 20A.

The medical diagnostic imaging system 30 consists mainly of a main unit 31 including a web browser 32, a pointing device 33 such as a trackball or a mouse, a display device 34 on which various images are displayed, and storage devices including a compact disk read-only memory (CD-ROM) drive 35, a magneto-optical disk (MOD) drive 36, and a hard disk 37.

The web browser 32 is, for example, Netscape Navigator (registered trademark of Netscape Communications Inc.).

At the user terminal 20A, a contract has been made for the use of the protocol/medical image database 12 included in each of the protocol management server 10J and 10U for the purpose of registration of a pair of a protocol and a medical image produced during scanning performed according to the protocol. Moreover, a contract has been made for the use of the contents of registration. A registering/utilizing subscriber program recorded on a storage medium (CD-ROM, MO, etc.) distributed from the manager of each of the protocol management servers 10J and 10U or a registering/utilizing subscriber program distributed over the network 1 is run in the user terminal 20A, whereby the user of the user terminal 20A is recognized as a registering/utilizing subscriber. The user of the user terminal 20A can register or utilize a protocol and medical image over the network 1.

At the user terminal 20B, a contract is made for the use of the protocol/medical image database 12 included in each of the protocol management servers 10J and 10U for the purpose of registration of a protocol and a medical image. A registering subscriber program recorded on a storage medium distributed from the manager of each of the protocol management servers 10J and 10U or a registering subscriber program distributed over the network 1 is run in the user terminal, whereby the user of the user terminal 20B is recognized as a registering subscriber. The user of the user terminal 20B can register a protocol and a medical image over the network 1.

At the user terminal 20C, a contract is made for the utilization of pairs of a protocol and a medical image registered using the protocol/medical image database 12 included in each of the protocol management servers 10J and 10U. A utilizing subscriber program recorded on a storage medium distributed from the manager of each of the protocol management servers 10J and 10U or a utilizing subscriber program distributed over the network 1 is run in the user terminal, whereby the user of the user terminal 20C is recognized as a utilizing subscriber. The user of the user terminal 20C can utilize pairs of a protocol and a medical image over the network 1.

The protocol management servers 10J and 10U hold subscriber information. The subscriber information is produced or updated as described below.

(1) A new subscriber makes a contract with the manager of each of the protocol management servers 10J and 10U, and receives a storage medium on which a program dependent on the contents of a contract is saved, or downloads the program over the network 1.

(2) When the new subscriber installs the program and activates it for the first time, a request for update of subscriber information is automatically sent to the protocol management server 10J or 10U over the network 1. The protocol management server 10J or 10U appends information of the new subscriber to the subscriber information.

(3) When a subscriber cancels a contract, the protocol management server 10J or 10U deletes the information of the subscriber from the subscriber information.

Incidentally, the manager may charge a subscription fee at the time of making a contract. Moreover, the manager may charge a management fee for provision of a service such as maintenance and update of subscriber information at regular intervals of a certain period or irregularly. Moreover, the manager may sell the program.

FIG. 2 shows the structure of the protocol/medical image database 12.

In the protocol/medical image database 12, a date of registration, a type of image, a region, image data, a grade, a registering person, and a protocol (scanning technique or imaging parameters) are recorded in association with each protocol identifier. For example, when MRI is specified in a type-of-image column, a pulse sequence-related imaging technique such as the fast spin echo (FSE) imaging technique, gradient echo (GE) imaging technique, echo planar imaging (EPI) technique, or fast recovery fast spin echo (FRFSE) imaging technique is specified in an associated scanning-technique column within the protocol column. Moreover, imaging parameters including a longitudinal relaxation time (T1), a transverse relaxation time (T2), a repetition time (TR), and an echo time (TE) are specified in an associated imaging-parameters column within the protocol column.

Registration to be achieved by recording data will be described with reference to FIG. 4 and FIG. 5 later.

FIG. 3 shows the structure of the subscriber information database 13.

In the subscriber information database 13, whether permission to download a protocol identified with a protocol identifier is granted is specified for each subscriber. In the illustrated example, the permission to download a protocol identified with P001 is granted to hospitals A and C but not granted to hospital B.

Figure 4:
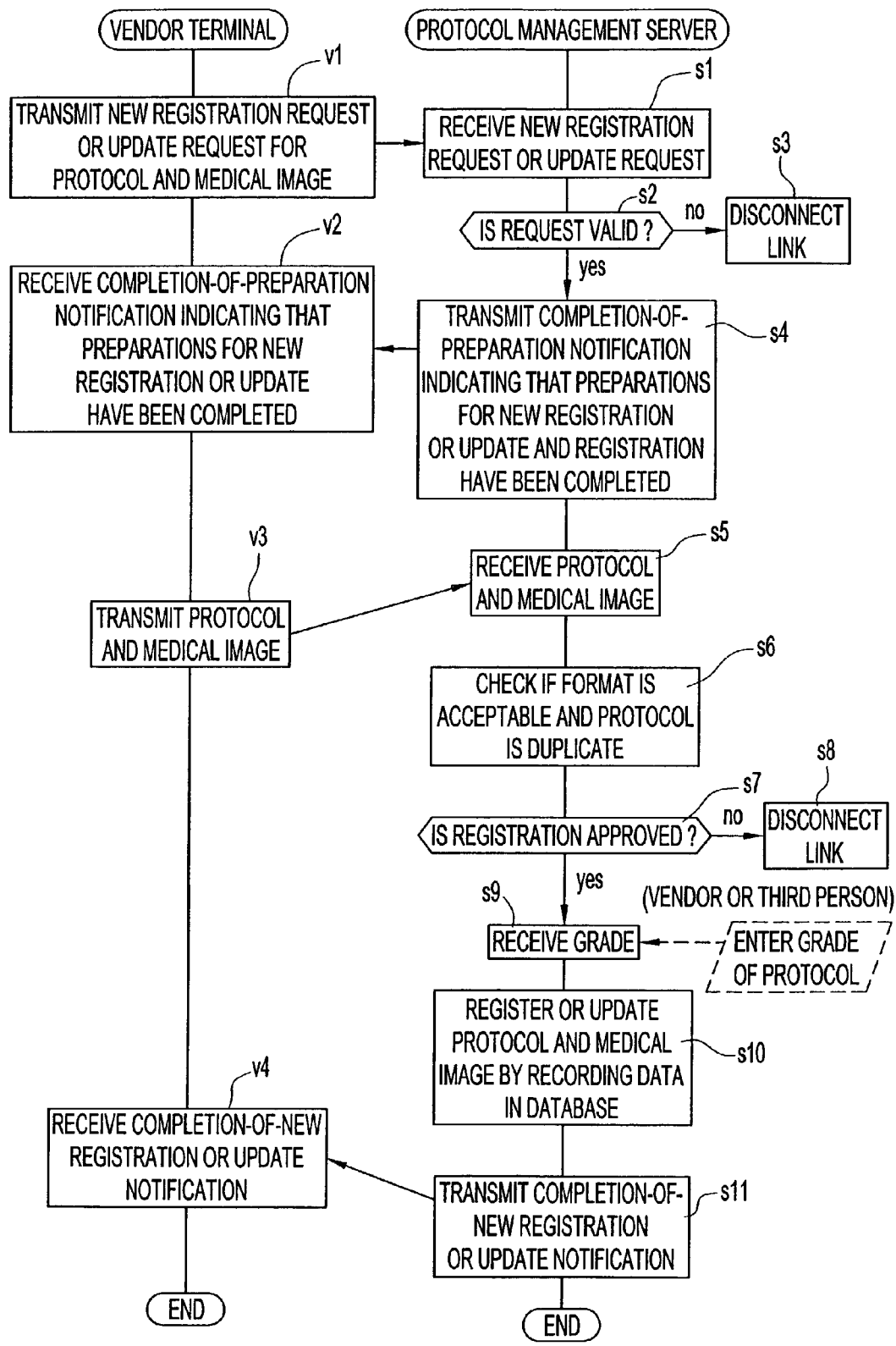
FIG. 4 is a flowchart describing a procedure according to which a protocol and a medical image are registered by recording data in a protocol/medical image database.

FIG. 4 is a flowchart describing a procedure according to which the vendor terminal 2 is used to register a protocol and a medical image by recording data in the protocol/medical image database 12. The flowchart on the left side of FIG. 4 describes actions to be performed by the vendor terminal 2, while the flowchart on the right side thereof describes actions to be performed by the protocol management server 10J or 10U.

Assume that an operator instructs new registration or update of a protocol and a medical image produced using the protocol. At step v1, the vendor terminal 2 transmits a new registration request or an update and register request for the pair of the protocol and medical image to both or either of the protocol management servers 10J and 10U.

At step s1, the protocol management server 10J or 10U receives the registration request.

At step s2, the protocol management server 10J or 10U checks the validity of the registration request. If the registration request is invalid, control is passed to step s3. If the registration request is valid, control is passed to step s4. The validity check is achieved according to a known method adopted when a system is connected on a communication line, such as, a method of checking a network address or a telephone number, a method of checking a password, or a method of checking an ID card.

At step s3, the communication link is disconnected.

At step s4, a completion-of-preparation notification indicating that preparations for new registration or update have been completed is transmitted to the vendor terminal 2.

At step v2, the vendor terminal 2 receives the completion notification.

At step v3, the protocol and medical image are transmitted to the protocol management server 10J or 10U over the network 1.

At step s5, the protocol management server 10J or 10U receives the protocol and medical image.

At step s6, the protocol is checked to see if the format is acceptable or the protocol is a duplicate of another. Specifically, the protocol is checked to see if the contents of the protocol satisfy specifications or whether exactly the same protocol has already been registered.

At step s7, the protocol management server 10J or 10U judges whether or not to approve registration. If registration is not approved, control is passed to step s8. If registration is approved, control is passed to step s9. For example, if an error from the specifications or exactly the same protocol is found out, registration is not approved.

At step s8, the communication link is disconnected.

At step s9, the protocol management server 10J or 10U receives a grade entered by a grader such as a vendor or a third person (for example, a physician or paramedic). The grader comprehensively assesses the image quality of a medical image, a scan time, a patient dose of electromagnetic waves or radiation, the clinical usefulness of the medical image, and others. The grader then determines a grade that reflects the use value of the protocol.

At step s10, the protocol management server 10J or 10U newly registers or updates the protocol and medical image by recording a protocol identifier, which is assigned to the protocol, and image data, which represents the medical image, in the protocol/medical image database 12 (see FIG. 2). Moreover, the date of registration, the type of medical image, the region, and the grade, and the registering person (these information items are specified in data sent from the user terminal 20A if necessary) are recorded.

At step s11, a new registration or update completion notification indicating that new registration or update has been completed is transmitted to the vendor terminal 2 over the network 1.

At step v4, the vendor terminal 2 receives the completion notification.

Figure 5:
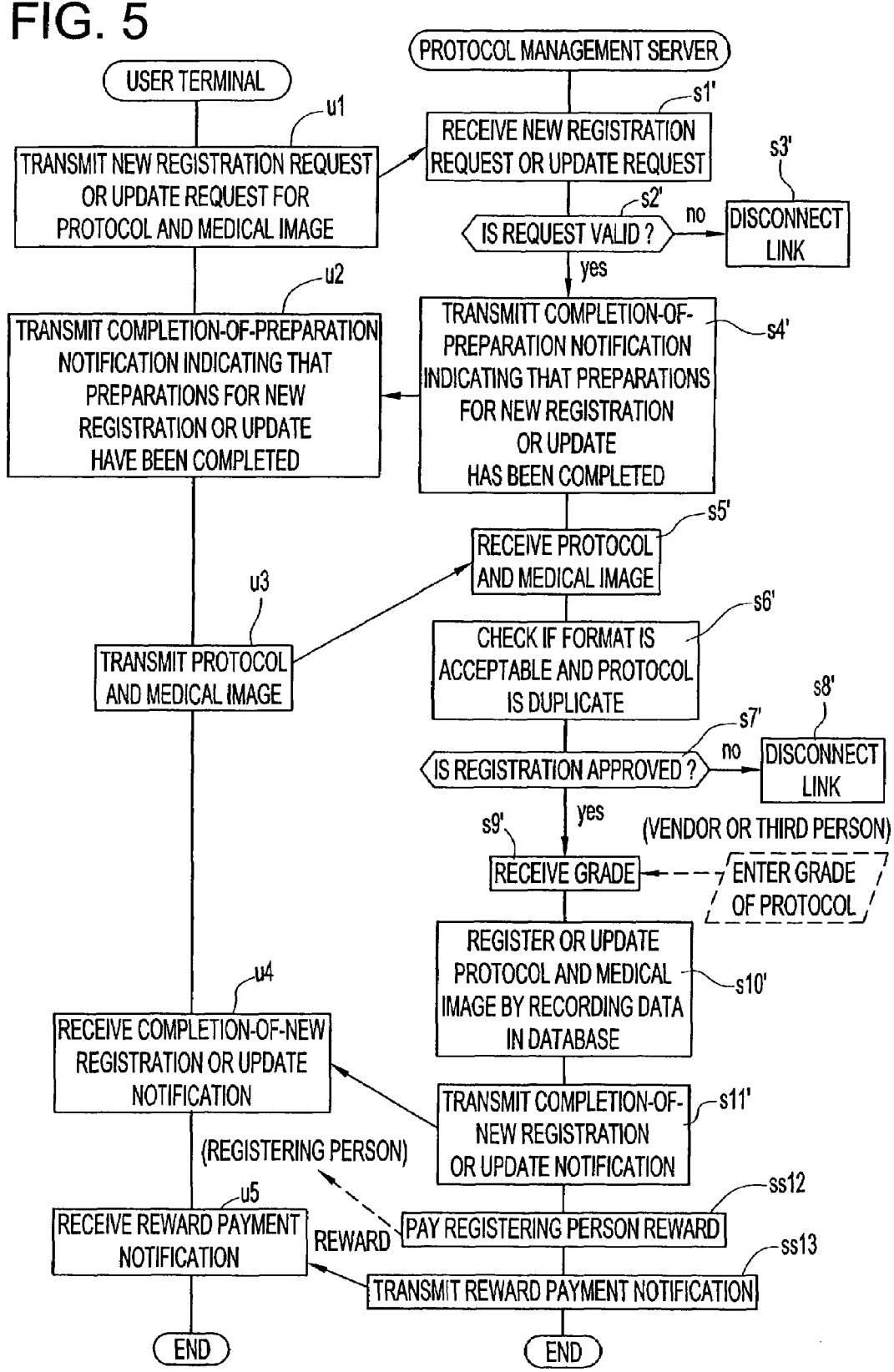
FIG. 5 is another flowchart describing a procedure according to which a protocol and a medical image are registered by recording data in a protocol/medical image database.

FIG. 5 is a flowchart describing a procedure according to which a user terminal (presumably the user terminal 20A) whose user is recognized as a registering subscriber is used to register a protocol and a medical image by recording data in the protocol/medical image database 12. The flowchart on the left side of FIG. 5 describes actions to be performed by the user terminal 20A, while the flowchart on the right side thereof describes actions to be performed by the protocol management server 10J or 10U.

Steps u1 to u4 are identical to steps v1 to v4 described in FIG. 4.

Steps s1' to s11' are identical to steps s1 to s11 described in FIG. 4.

However, the vendor terminal 2 should be read as the user terminal 20A in the description of the procedure.

At step ss12, the protocol management server 10J or 10U pays the registering person (the user of the user terminal 20A) a reward dependent on the grade. For example, money is paid in to a bank account of the user over the network 1.

At step ss13, a reward payment notification (for example, a date of payment and a charge) is transmitted to the user terminal 20A over the network 1.

At step u5, the user terminal 20A receives the reward payment notification, and displays a message concerning reward payment on the display device 34.

Figure 6:
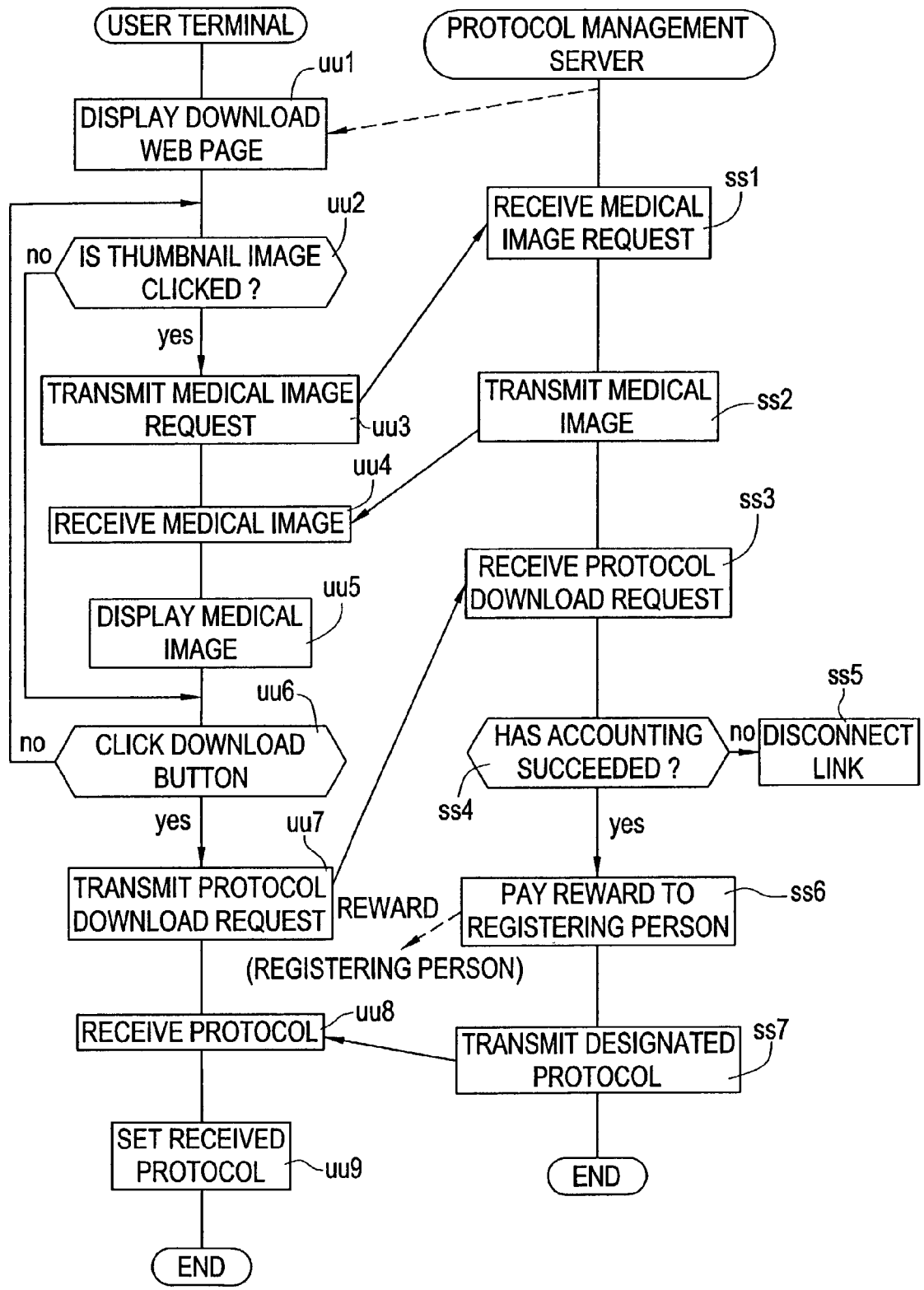
FIG. 6 is a flowchart describing a procedure according to which a protocol and a medical image registered using a protocol/medical image database is utilized.

FIG. 6 is a flowchart describing a procedure according to which a user terminal whose user is recognized as a utilizing subscriber (presumably the user terminal 20A) is used to utilize a protocol and a medical image that are registered using the protocol/medical image database 12. The flowchart on the left side of FIG. 6 describes actions to be performed by the user terminal 20A, while the flowchart on the right side thereof describes actions to be performed by the protocol management server 10J or 10U.

At step uu1, the user terminal 20A activates the web browser 32 installed in the medical diagnostic imaging system 31, accesses the web server 11 over the network 1, and displays a download web page G1 on the display device 34. As shown in FIG. 7, the download web page G1 contains, for example, dates of registration, regions, thumbnail images of medical images, grades, registering persons, a protocol list, download buttons, a condition retrieval button, and a cancel button.

At step uu2, if any thumbnail image in the download web page G1 is clicked at the user terminal 20A, control is passed to step uu3. Otherwise, control is passed to step uu6.

At step uu3, a request for a medical image relevant to the thumbnail image is transmitted to the protocol management server 10J or 10U over the network 1.

At step ss1, the protocol management server 10J or 10U receives the medical image request.

At step ss2, the medical image relevant to the thumbnail image is read from the protocol/medical image database 12 and transmitted to the user terminal 20A over the network 1.

At step uu4, the user terminal 20A receives the medical image.

At step uu5, the user terminal 20A displays the medical image on the display device 34. The user judges from the medical image whether the protocol concerned is worth being utilized.

At step uu6, if any download button in the download web page G1 is clicked at the user terminal 20A, control is passed to step uu7. Otherwise, control is returned to step uu2.

At step uu7, a request for download of a designated protocol is transmitted to the protocol management server 10J or 10U over the network 1.

At step ss3, the protocol management server 10J or 10U receives the protocol download request.

At step ss4, the user of the user terminal 20A or the decision-making body owning the user terminal 20A is charged a use fee for the protocol. If accounting succeeds, control is passed to step ss6. Otherwise, control is passed to step ss5. For example, a bill screen image that is not shown is displayed on the display device 34 included in the user terminal 20A in order to charge a use fee. If a user maneuvers to pay in from his/her bank account, to pay using a credit card, or to pay using a payment agent service, it is judged that accounting has succeeded.

At step ss5, the communication link is disconnected.

At step ss6, the registering person (the user of the use terminal 20 who has registered the protocol) is paid a reward for the download. Incidentally, the reward may be identical to the use fee or may be calculated by subtracting a commission from the use fee.

At step ss7, the designated protocol is transmitted to the user terminal 20A over the network 1.

At step uu8, the user terminal 20A receives the protocol.

At step uu9, the user terminal sets the received protocol in the medical diagnostic imaging system 30. Consequently, scanning can be immediately performed based on the protocol.

If the condition retrieval button in the download web page G1 (see FIG. 7) is clicked, conditions including a region, a purpose of use, a grade (for example, a grade of 80 or higher), a merit (for example, high contrast), and a scan time (for example, 30 sec or less) may be designated. In this case, only protocols selected under the conditions are presented as options for download. These actions are not described in the flowchart of FIG. 6.

According to the protocol utilization system 100, a pair of a protocol and a medical image sent from the vendor terminal 2 and a user terminal 20 over the network 1 is registered by recording data in the protocol/medical image database 12 included in the protocol management server 10J or 10U. Numerous protocols and medical images can be efficiently managed on a centralized basis. Moreover, the protocols and medical images registered using the protocol/medical image database 12 can be shared by the plurality of user terminals 20.

Other Embodiments

The features of the protocol utilization system 100 may be modified as described below.

(1) At step ss4 in FIG. 6, every time a protocol is downloaded to the user terminal 20, the user of the protocol is charged a use fee. Instead or in addition, every time the protocol is used (to perform scanning), the use fee may be charged.

(2) A protocol download history or a protocol use history may be recorded in the user terminal 20. The protocol management server 10J or 10U may perform accounting according to the history. For example, the protocol management server 10J or 10U successively accesses the user terminals 20 over the network 1 regularly (for example, every other month) or irregularly (for example, on a day designated by the manager), and receives the history. Otherwise, the user terminal 20 transmits the history to the protocol management server 10J or 10U over the network 1.

(3) Protocols that can be transmitted to the user terminals 20 may be protocols having the term of validity or the number of times of use limited. In this case, diverse needs including a need for trial and evaluation and a need for temporary use can be coped with.

(4) Protocols that can be transmitted to the user terminals 20 may be limited in compliance with the legal conditions established at the installation site of the user terminals 20. Thus, accidental download of a protocol that does not comply with the legal conditions can be prevented. For example, protocol management servers accessible to the user terminals 20 may be limited to the protocol management servers 10 installed in a district within which the same legal conditions are applied (for example, in the same nation). Only protocols that comply with the legal conditions established in the district can be registered in the protocol management server 10. Otherwise, in the subscriber information database 13 included in the protocol management server 10 (see FIG. 3), Not Granted may be forcibly specified in the permission-to-download-a-protocol column associated with a protocol identifier assigned to a protocol that does not comply with the legal conditions established at the installation site of the user terminal 20 used by a subscriber.

(5) If a protocol is newly registered or updated, the protocol management server 10J or 10U may notify the user terminals 20 of the fact over the network 1. Thus, the users of the user terminals 20 become immediately aware of the fact that a new protocol can be downloaded.

(6) The protocol management server 10J or 10U may respond to a download request sent from a non-subscriber (a user who has not made a contract) 60. Thus, a protocol utilization service can be provided for a large number of users (customers). However, a registration request from the non-subscriber 60 is not responded to in efforts to keep the contents of registration or the contents of the protocol/medical image database 12 highly reliable.

Many widely different embodiments of the invention may be configured without departing from the spirit and the scope of the present invention. It should be understood that the present invention is not limited to the specific embodiments described in the specification, except as defined in the appended claims.

The invention claimed is:

1. A protocol/medical image registration system comprising:
   a vendor terminal managed by a vendor;
   a protocol management server connected to said vendor terminal, wherein if an operator instructs new registration or update of a medical image and a protocol executed by a medical imaging system to generate the medical image, said vendor terminal transmits a new registration request including the new registration or an update request including the update via a network to said protocol management server;
   in response to the registration request, said protocol management server newly registers or updates the protocol and medical image, which are sent from said vendor terminal, by recording data in a database; and
   a user terminal configured to receive a determination whether to download the protocol from said protocol management server based on multiple levels of usefulness that are displayed by said user terminal and that include a grade value of the protocol received from a grader, the grader determining the grade value representative of a use value of the protocol based on a comprehensive assessment of the medical image, wherein the grade value is used to determine a monetary reward rewarding a provider of the protocol, wherein said protocol management sewer is configured to deny, to a user, a download of the protocol configured to generate an echo to generate the medical image, wherein said protocol management server is configured to deny the download of the protocol based on a legal condition established in a geographical region including said user terminal.

2. A protocol/medical image registration system according to claim 1, wherein the grade value is determined based on at least one of a quality of the medical image, a scan time, and a patient dose of radiation.

3. A protocol/medical image registration system according to claim 1, wherein said protocol management sewer is configured to record a protocol identifier assigned to the protocol and image data representative of the medical image.

4. A protocol/medical image registration system according to claim 1, wherein said protocol management sewer is configured to record at least one of a date of registration, a type of medical image, a region, the grade value, and a registering person.

5. A protocol/medical image registration system according to claim 1, wherein said user terminal further comprises a display device, said user terminal further configured to download a web page on said display device.

6. A protocol/medical image registration system according to claim 5, wherein said web page comprises at least one of a date of registration, a region, a thumbnail image of the medical image, and the grade value.

7. A medical image provision system comprising:
   a vendor terminal managed by a vendor;
   a protocol management sewer connected to said vendor terminal;
   a user terminal; and a network over which said protocol management sewer and said user terminal are interconnected, wherein if an operator instructs new registration or update of a medical image and a protocol executed by a medical imaging system to generate the medical image, said vendor terminal or user terminal transmits a new registration request including the new registration or an update request including the update via said network to said protocol management sewer;

in response to the registration request, said protocol management sewer newly registers or updates the protocol and medical image, which are sent from said vendor terminal or user terminal, by recording data in a database;

if an operator instructs acquisition of the medical image, said user terminal transmits an image request to said protocol management sewer;

in response to the image request, said protocol management sewer reads the medical image from said database and transmits it to said user terminal; and said user terminal receives the medical image and displays it on a screen included therein, and said user terminal configured to receive a determination whether to download the protocol from said protocol management sewer based on multiple levels of usefulness that are displayed by said user terminal and that include a grade value of the protocol received from a grader, the grader determining the grade value representative of a use value of the protocol based on a comprehensive assessment of the medical image, wherein the grade value is used to determine a monetary reward rewarding a provider of the protocol, wherein said protocol management sewer is configured to deny, to a user, a download of the protocol configured to generate an echo to generate the medical image, wherein said protocol management server is configured to deny the download of the protocol based on a legal condition established in a geographical region including said user terminal.

8. A medical image provision system according to claim 7, wherein said user terminal further comprises a display device, said user terminal further configured to download a web page on said display device, said web page comprising at least one of a date of registration, a region, a thumbnail image of the medical image, and the grade value.

9. A protocol utilization system comprising:
a vendor terminal managed by a vendor;
a protocol management server connected to said vendor terminal;
a user terminal; and
a network over which said protocol management server and said user terminal are interconnected, wherein if an operator instructs new registration or update of a medical image and a protocol executed by a medical imaging system to generate the medical image, said vendor terminal or user terminal transmits a new registration request including the new registration or an update request including the update via said network to said protocol management server;

in response to the registration request, said protocol management server newly registers or updates the protocol and medical image, which are sent from said vendor terminal or user terminal, by recording data in a database;

if an operator instructs utilization of the protocol, said user terminal transmits a protocol download request to said protocol management server;

in response to the protocol download request, said protocol management server reads the protocol from said database and transmits it to said user terminal; and said user terminal sets the received protocol in a medical diagnostic imaging system, and said user terminal configured to receive a determination whether to download the protocol from said protocol management server based on multiple levels of usefulness that are displayed by said user terminal and that include a grade value of the protocol received from a grader, the grader determining the grade value representative of a use value of the protocol based on a comprehensive assessment of the medical image, wherein the grade value is used to determine a monetary reward rewarding a provider of the protocol, wherein said protocol management server is configured to deny, to a user, a download of the protocol configured to generate an echo to generate the medical image, wherein said protocol management server is configured to deny the download of the protocol based on a legal condition established in a geographical region including said user terminal.

10. A protocol utilization system according to claim 9, wherein a protocol download history or a protocol use history is recorded in said user terminal that has received the protocol.

11. A protocol utilization system according to claim 10, wherein said protocol management server successively accesses said user terminal over said network and receives the download history or use history from said user terminal.

12. A protocol utilization system according to claim 10, wherein said user terminal transmits the download history or use history to said protocol management server over said network.

13. A protocol utilization system according to claim 9, wherein a plurality of protocol management servers is included, and the protocol management servers are accessible to said user terminal.

14. A protocol utilization system according to claim 9, wherein when a protocol is newly registered or updated, said protocol management server notifies said user terminal of the fact over said network.

15. A protocol utilization system according to claim 9, wherein said protocol management server responds to a download request sent from a user terminal at which no contract is made for utilization of protocols, but does not respond to a registration request sent therefrom.

16. A protocol utilization system according to claim 9, wherein said medical diagnostic imaging system is a least one of an MRI system, an X-ray CT system, a diagnostic ultrasound system, a PET system, a radiography system, and a CR system.

17. A protocol utilization system according to claim 16, wherein if said medical diagnostic imaging system is an MM system, the protocol refers to at least one of a pulse sequence-related imaging technique and imaging parameters.

18. A protocol utilization system according to claim 9, wherein said protocol management server is configured to record at least one of a date of registration, a type of medical image, a region, the grade value, and a registering person.

19. A protocol utilization system according to claim 9, wherein said user terminal further comprises a display device, said user terminal further configured to download a web page on said display device, said web page comprising at least one of a date of registration, a region, a thumbnail image of the medical image, and the grade value.

* * * * *